United States Patent
Chuang

(10) Patent No.: US 6,429,778 B1
(45) Date of Patent: Aug. 6, 2002

(54) WATER-MONITORING APPARATUS CAPABLE OF AUTO-TRACING WATER LEVEL AND NON-CONTACT SIGNAL RELAY FOR THE SAME

(75) Inventor: Hsu-Chen Chuang, Taipei (TW)

(73) Assignee: Hycom Instruments Corp., Taipei (TW)

( * ) Notice: Subject to any disclaimer, the term of this patent is extended or adjusted under 35 U.S.C. 154(b) by 0 days.

(21) Appl. No.: 09/960,567

(22) Filed: Sep. 21, 2001

(30) Foreign Application Priority Data

Sep. 27, 2000 (TW) .......................................... 89216855

(51) Int. Cl.[7] .............................................. G08B 21/00
(52) U.S. Cl. ...................... 340/623; 340/612; 340/618; 340/624; 73/170; 73/292
(58) Field of Search ................................ 340/623, 603, 340/612, 618, 619, 624, 625, 566, 601; 73/291, 292, 305, 306, 307, 319

(56) References Cited

U.S. PATENT DOCUMENTS

| | | | |
|---|---|---|---|
| 4,448,068 A | * | 5/1984 | Sutherland et al. ........... 73/170 |
| 4,557,608 A | * | 12/1985 | Carver ........................ 374/170 |
| 4,922,226 A | * | 5/1990 | Hsieh et al. ................. 340/521 |
| 5,186,253 A | * | 2/1993 | Gustafson et al. ............ 166/77 |
| 6,185,988 B1 | * | 4/2000 | Baxter, Jr. ................. 73/53.01 |
| 6,131,659 A | * | 10/2000 | Johnson .................. 166/250.05 |
| 6,175,809 B1 | * | 1/2001 | Naville ........................ 702/14 |

* cited by examiner

Primary Examiner—Daniel J. Wu
Assistant Examiner—Phung Nguyen
(74) Attorney, Agent, or Firm—Connolly Bove Lodge & Hutz

(57) ABSTRACT

A water-monitoring apparatus includes a frame installed by water. A reel is mounted on the frame. A cable including lower and upper ends is wound on the reel. A buoy is connected with the cable. At least one sensor is used to detect a water quality parameter and to produce a signal representative of the water quality parameter. The at least one sensor is carried via the buoy and electrically connected with the lower end of the cable. The reel can be rotated to adjust a length of the cable extending from the reel so that the at least one sensor can always be immersed in the water. A signal relay includes a first block electrically connected with the at least one sensor and a second block electrically connected with a monitoring station wherein the first and second blocks are connected with each other in a non-contact electric manner.

32 Claims, 5 Drawing Sheets

WATER-MONITORING APPARATUS CAPABLE OF AUTO-TRACING WATER LEVEL AND NON-CONTACT SIGNAL RELAY FOR THE SAME

BACKGROUND OF INVENTION

1. Field of Invention

The present invention is directed to monitor water quality and, more particularly, to a water-monitoring apparatus for detecting water quality parameters at constant depths.

2. Related Prior Art

While developing, the world is encountering a more and more serious problem of pollution. Water pollution could be the worst among all kinds of pollution. More and more pollutants are dumped to reservoirs and open channels from fixed sources, e.g., factories and farms, or from mobile sources, e.g., vehicles. Such pollutants may be released into water directly, or may be washed into the water by rain. Once introduced into the water, such pollutants inevitably increase costs in treating the water and very often harm human bodies, life stock and aquatic lives.

Before any proper measure can be taken to solve the problem of water pollution, by what pollutants and to what extent the water is polluted must be figured out. In other words, various quality parameters of the water must be monitored. Some water analyses are performed manually, however they are cumbersome.

As to continuous water analysis, there have been installed some conventional monitoring stations into which water is automatically pumped through pipes. It, however, is found difficult to have the pipes catch up with the water level changing vigorously from season to season. When the water level becomes too low for the pipes to reach, it is impossible to pump water through the pipes.

To make sure that the water can be monitored continuously, there have been devised some water-monitoring apparatuses in which sensors are carried by means of a buoy tied to a bank or a well by means of a cable. To have the buoy float on the water when the water level is low, a sufficiently long cable is used. However, the cable allows the buoy to drift for a long distance in any direction when the water level is high. As the buoy drifts, the cable often tangles with miscellaneous objects, e.g., twigs. This could seriously affect the operation of the sensors. For example, the buoy and therefore the sensors may be kept away from the water due to the cable tangling with a twig reaching out from the water, thus causing a failure.

To prevent the cable from tangling with miscellaneous objects, there has been devised a length control device in which the cable is wound on a reel operatively connected with a motor. The motor can be activated to rotate the reel to adjust a length of the cable extending from the reel so that the sensors can always be immersed in water. However, the motor consumes a lot of energy.

In addition, to transmit signals from the sensors to a monitoring station, the cable is connected to the monitoring station through a signal relay including a mandrel electrically connected with the cable. The mandrel rotates together with the reel. The signal relay further includes a brush electrically connected with the monitoring station. The brush does not rotate. The mandrel is in rotational engagement with the brush, thus allowing the mandrel to rotate with respect to the brush while allowing the signals to be transmitted from the mandrel to the brush. However, friction between the mandrel and the brush interferes with the rotation of the reel and wears out the brush after serving for a period of time.

Therefore, the present invention is intended to alleviate or even obviate the drawbacks that are encountered in the prior art.

SUMMARY OF INVENTION

It is the primary objective of the present invention to provide a water-monitoring apparatus capable of automatically tracing water level.

It is another objective of the present invention to provide a water-monitoring apparatus with a tangle-free sensor-carrying cable.

It is another objective of the present invention to provide a water-monitoring apparatus with a sensor-carrying cable of an automatically adjustable length.

It is another objective of the present invention to provide a water-monitoring apparatus with a sensor-carrying cable wound on a reel capable of automatic rotation for adjusting a length of the sensor-carrying cable extending from the reel.

It is another objective of this invention to provide a non-contact signal relay for use in a reel structure to facilitate transmitting electric signals from an electric information source attached to the reel structure to a monitoring station without a rotational intervention.

In accordance with an aspect of the present invention, a water-monitoring apparatus includes a frame installed on a well or a bank by water. A reel is mounted on the frame. A constant torque device is used to exert a constant torque on the reel. A cable including a lower end and an upper end is wound on the reel. A buoy is connected with the cable. A detecting device includes at least one sensor. The detecting device is carried via the buoy and electrically connected with the lower end of the cable. The detecting device is used for detecting at least one water quality parameter. A signal relay is electrically connected with the upper end of the cable for receiving an electric signal from the detecting device.

In accordance with another aspect of the present invention, a non-contact signal relay is used in a water-monitoring apparatus. In the water-monitoring apparatus, a frame is installed in a proper position by water. A reel is mounted on the frame. A cable is wound on the reel so that the reel rotates as the cable travels. The cable includes lower and upper ends. A buoy is connected with the cable. At least one sensor is used to detect a water quality parameter and to produce a signal representative of the water quality parameter. The at least one sensor is carried via the buoy and electrically connected with the lower end of the cable. The reel can be rotated to adjust a length of the cable extending from the reel so that the at least one sensor can always be immersed in the water. The non-contact signal relay includes a first block electrically connected with the at least one sensor and a second block electrically connected with a monitoring station wherein the first and second blocks are connected with each other in a non-contact electric manner.

The first block of the signal relay includes an emitter for emitting the signals. The second block of the signal relay includes a second circuit board attached to the frame and electrically connected with a monitoring station and a receiver installed on the second circuit board for receiving the signals.

DETAILED DESCRIPTION OF INVENTION

Figure 1:
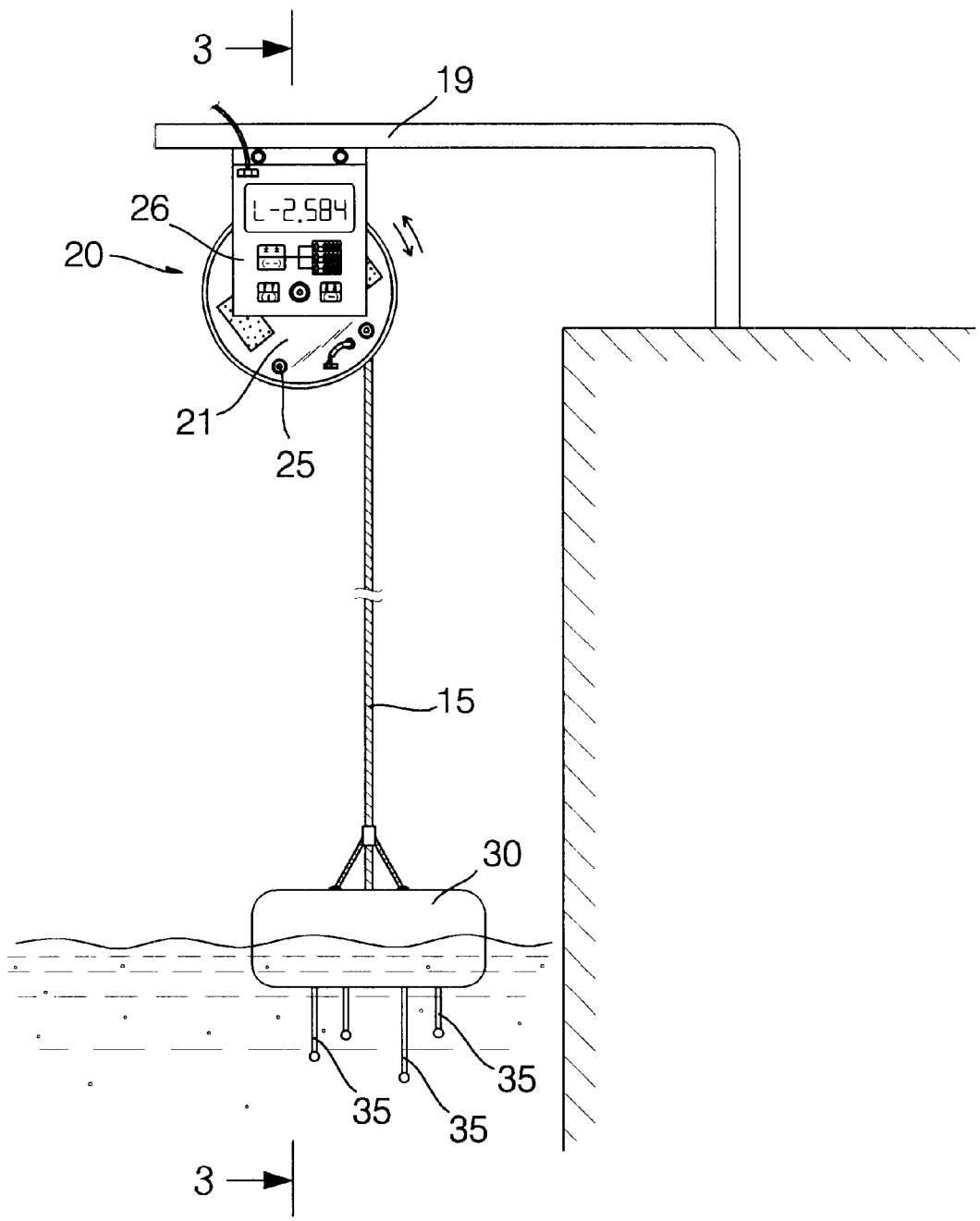
FIG. 1 is a front view of a water-monitoring apparatus in accordance with the present invention.

Referring to FIG. 1, a water-monitoring apparatus according to an embodiment of the present invention is shown. The water-monitoring apparatus is installed in an appropriate position by water so that at least one sensor 35 thereof is placed in the water for detecting at least one water quality parameter. For example, the water-monitoring apparatus may be installed on a bank of an ocean, a lake, a river, a groove and a trench or on a well.

The water-monitoring apparatus includes a frame 19 for supporting other components (to be described) thereof The frame 19 includes a first end firmly attached to the bank and a second end extending to a position above the water surface.

Figure 3:
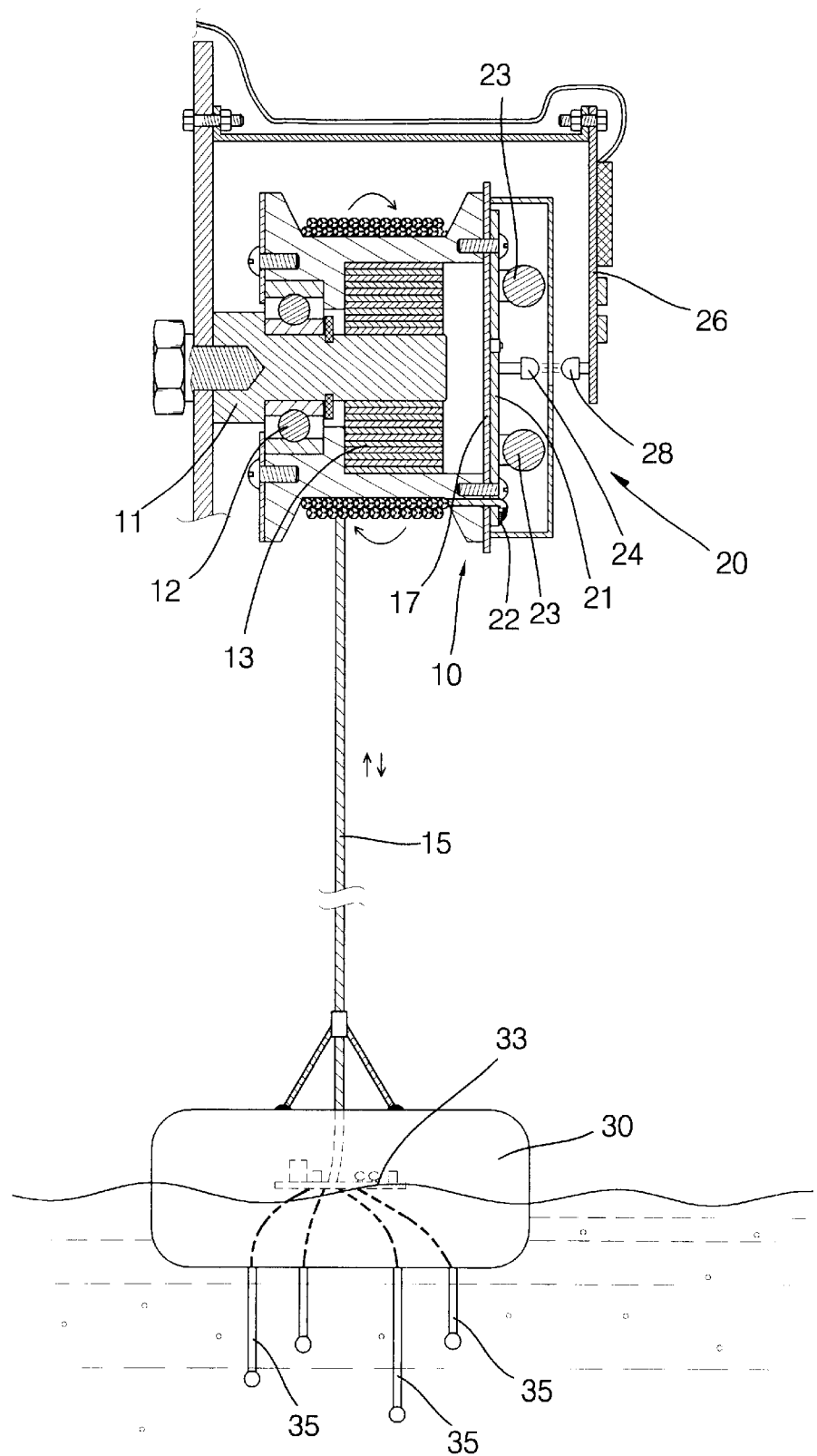
FIG. 3 is a cross-sectional view taken along line 3—3 in FIG. 1.

Referring to FIG. 3, a shaft 11 is mounted on a plate (not numbered) firmly attached to the frame 19. The shaft 11 includes a first end defining a threaded cavity for engagement with a threaded bolt (not numbered) inserted through a hole, (not numbered) defined in the plate. Thus, the shaft 11 is firmly attached to the plate.

A reel 10 is mounted on a middle section of the shaft 11 via a bearing 12 so that the reel 10 is allowed to rotate with respect to the shaft 11. The reel 10 includes a cylindrical body and two flanges each formed at an end of the cylindrical body.

A coil spring 13 is connected between the shaft 11 and the reel 10. The coil spring 13 includes a first end and a second end. The first end of the coil spring 13 is attached to a second end of the shaft 11 and the second end of the coil spring 13 is attached to the reel 10. Thus, the coil spring 13 can exert a torque on the reel 10. The coil spring 13 is selected so that when deformed within a certain range it provides a substantially constant torque to the reel 10.

A cable 15 is wound on the reel 10. The cable 15 includes an upper end and a lower end. The upper end of the cable 15 is inserted through a hole (not numbered) defined in one of the flanges of the reel 10. Thus, the upper end of the cable 15 can be connected with a signal relay 20 (to be described in detail later) electrically linked to a monitoring station.

A buoy 30 is connected with the cable 15. The buoy 30 defines an internal space (not numbered) and an upper hole (not shown) so that some elements (to be described) can be put into the buoy 30 through the holes defined therein.

Attached to the buoy 30 are a number of sensors 35. Each sensor 35 includes a cylindrical body (not numbered) attached to the buoy 30. Each sensor 35 is adapted for producing a primary signal representative of an environmental parameter and, more particularly, a water quality parameter such as pH, temperature, oxygen content, conductivity, chlorine content, turbidity, heavy metal content, etc. The sensors 35 may be kept at different distances or at a same distance from the buoy 30. Generally, the sensors 35 are used to detect different water quality parameters; however, some or all of them can be used to detect a same water quality parameter.

Electrically connected with the sensors 35 is a circuit board 33. The circuit board 33 is received in the buoy 30. Each sensor 35 is electrically connected with the circuit board 33 via a wire (not numbered) inserted through the cylindrical body thereof and one of the lower holes defined in the buoy 30. The circuit board 33 is used to convert the primary signal to an electric signal that is transmitted to the monitoring station through the signal relay 20. Moreover, the circuit board 33 is electrically connected with the lower end of the cable 15 inserted through the upper hole defined in the buoy 30. The upper hole defined in the buoy 30 is then sealed to protect the circuit board 33 from water.

In use, the buoy 30 is deployed on the water surface so that the sensors 35 are immersed in the water for detecting various qualities of the water. The buoy 30 floats on the water surface. While floating, the buoy 30 is subject to the gravity, a floating force exerted by the water and a tensile force exerted by the cable 15. There is a balance between these forces.

The tensile force exerted by the cable 15 results from the torque exerted on the reel 10 by the coil spring 13. As mentioned, when deformed within a range, the coil spring 13 exerts a substantially constant torque on the reel 10. Thus, when the length of the cable 15 extending from the reel 10 changes within a range, the cable 15 exerts a substantially constant tensile force on the buoy 30.

When the water level changes, the length of the cable 15 extending from the reel 10 is accordingly adjusted while the cable 15 exerts a substantially constant tensile force on the buoy 30. Since the tensile force and the gravity exerted on the buoy 30 remain the same, the floating exerted on the buoy 30 remains the same in order to maintain the balance of forces. In other words, a substantially constant volume of the buoy 30 is immerged in the water. Accordingly the sensors 35 are immerged in the water at substantially constant depths.

Figure 2:
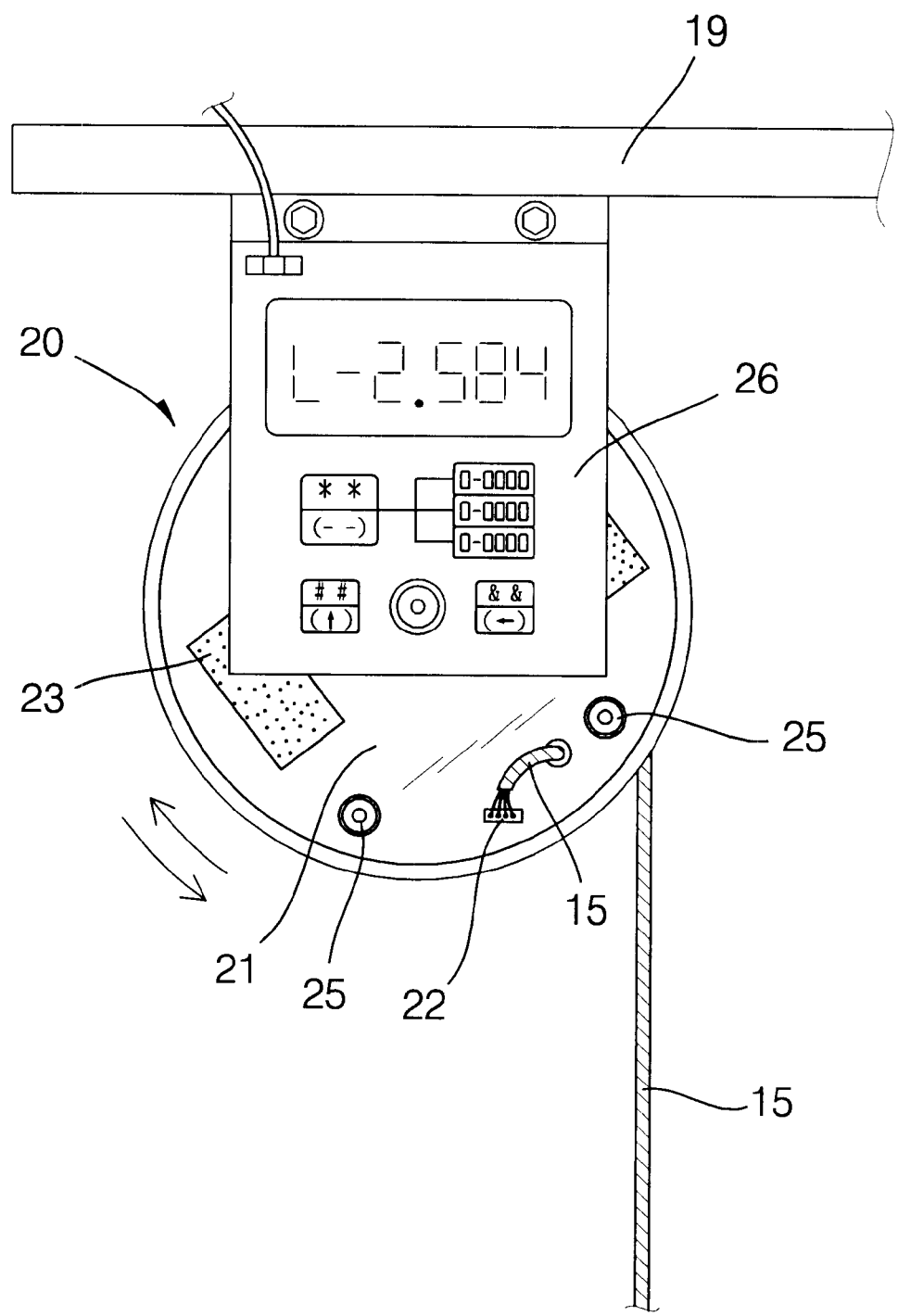
FIG. 2 is an enlarged view of a signal relay used in the water-monitoring apparatus shown in FIG. 1.

Now, the signal relay 20 will be described in detail. As shown in FIGS. 2 and 3, the signal relay 20 is a non-contact signal relay. The signal relay 20 includes a circuit board 21 attached to the reel 10. A connector 22 is formed on the circuit board 21 for engagement with the upper end of the cable 15. Thus, the primary signals can be transmitted from the circuit board 33 to the circuit board 21. Also installed on the circuit board 21 is a battery 23 for provision of power to the signal relay 20 and the circuit board 33 and components mounted on or connected with these boards. A light emitter 24 is also formed on the circuit board 21. The primary signals are transformed into optical signals by means of the light emitter 24. The optical signals are received by means of a light receiver 28 installed on a circuit board 26 attached to the frame 19. In turn, the circuit board 26 is electrically connected with the monitoring station.

The circuit board 33 is designed to periodically acquire the primary signals from the sensors 35, e.g., once every minute. For the rest of every minute, the circuit board 33 is kept in a power-saving mode. However, if necessary, the circuit board 33 can be actuated any time by pressing a button 25 formed on the circuit board 21 to acquire the primary signals from the sensors 35.

Figure 4:
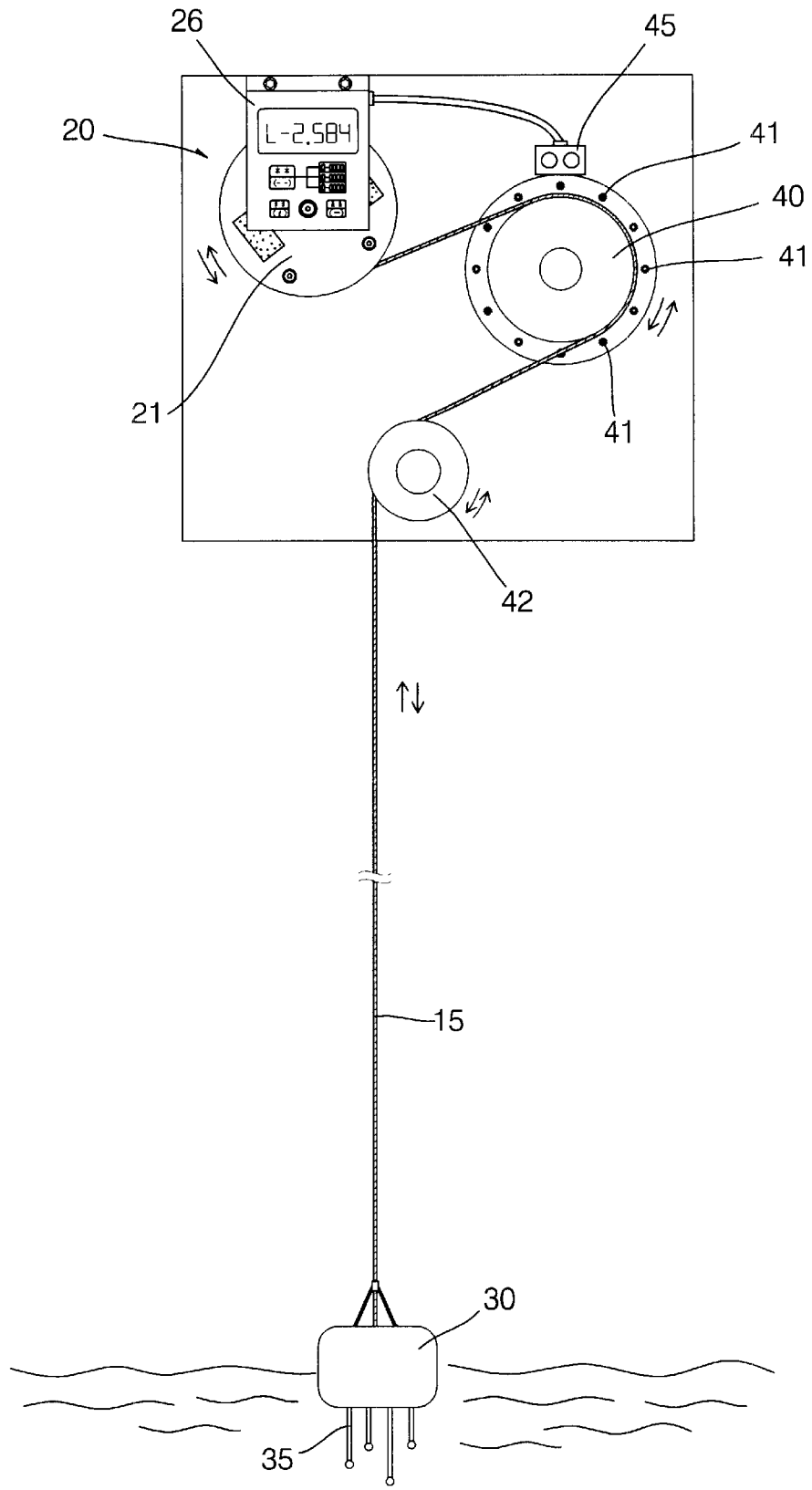
FIG. 4 is a front view of a water-monitoring apparatus in accordance with a second embodiment of the present invention.

Referring to FIG. 4, a second embodiment of the present invention is shown. The embodiment of FIG. 4 is identical to that of FIGS. 1 to 3 except for including a level-determining device for determining the water level. The level-determining device includes a pulley 40 mounted on the frame 19. A length of the cable 15 is wound on the pulley 40 so that the cable 15 rotates the pulley 40 as the buoy 30 rises or falls together with the water level. A number of magnets 41 are evenly arranged near or on the periphery of the pulley 40. A magnetic detector 45 is mounted on the frame 19 for detecting each magnet 41 passing by. When the water level changes, the buoy 30 moves up or down, thus causing the pulley 40 to rotate counter-clockwise or clockwise and the magnets 41 to move. The magnetic detector 45 detects how many magnets 41 pass by and in what direction in order to determine how much the water level rises or falls. The cable 15 is further wound on a pulley 42 mounted on the frame 19. Thus, the direction of the cable 15 is changed and the length of the cable 15 wound on the pulley 40 is increased so as to avoid the cable 15 sliding on the pulley 40.

Figure 5:
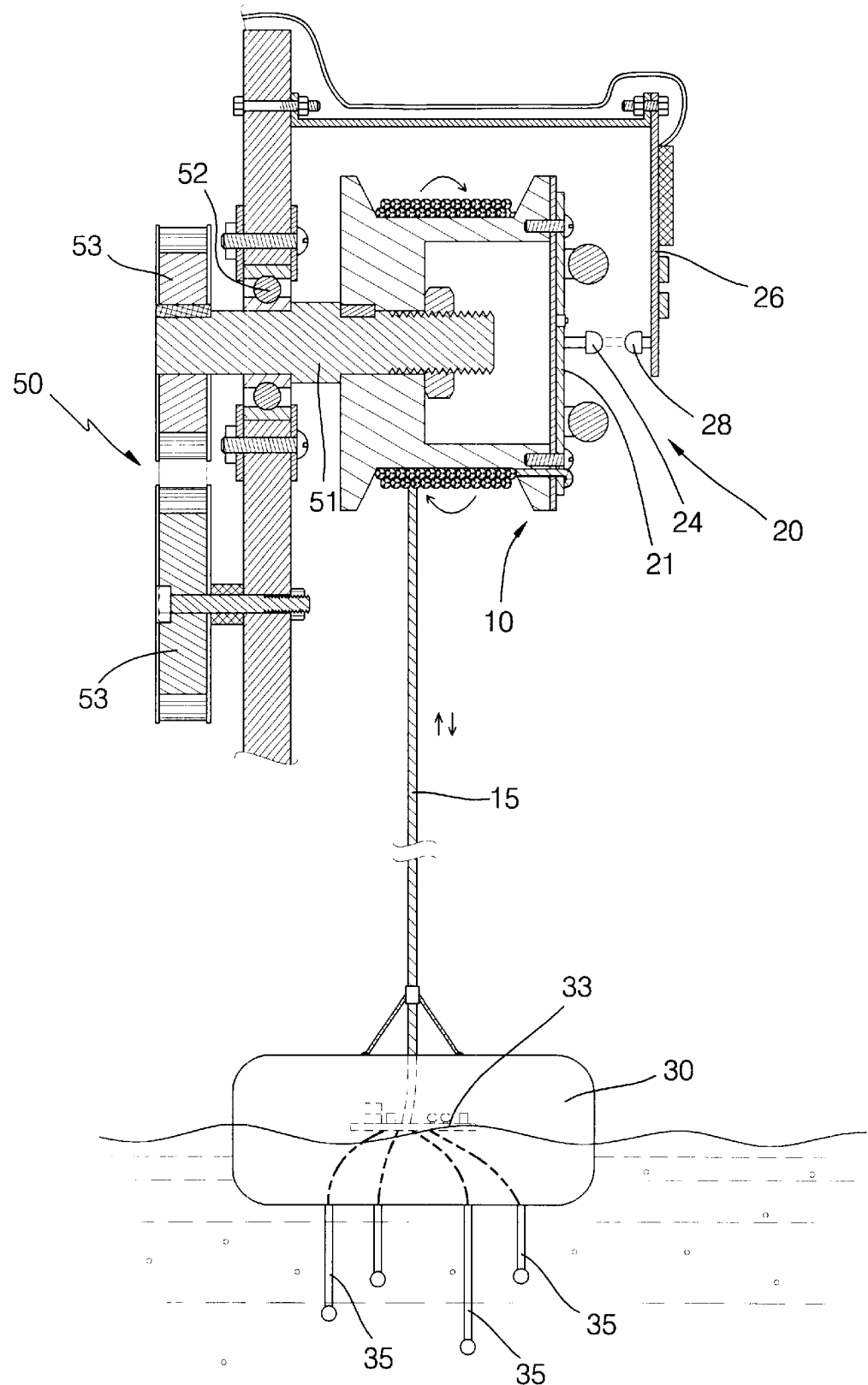
FIG. 5 is a front view of a water-monitoring apparatus in accordance with a third embodiment of the present invention.

Referring to FIG. 5, a third embodiment of the present invention is shown. A constant torque spring assembly 50 is used in the embodiment of FIG. 5 in order to substitute for the coil spring 13 of the embodiment of FIGS. 1 to 3. The constant torque spring assembly 50 includes an axle 51 mounted on the frame 19 by means of a bearing 52. The axle 51 is connected with the reel 10 so that they are allowed to rotate together. Furthermore, the axle 51 is connected with one of two drums 53 of the constant torque spring assembly 50. Thus, the constant torque spring assembly 50 exerts a constant torque on the reel 10 through the axle 51. The constant torque spring assembly 50 is known in the art and will not be described in further detail.

The present invention has been described in relation to several embodiments. It is obvious that modifications and variations can be derived from the above-described embodiments by those skilled in the art. For example, the circuit board 33 and the board 21 can be merged or integrated into one. The embodiments are described with reference to the drawings for illustrative purposes only and are not intended to limit the scope of the present invention that can only be limited by the attached claims.

What is claimed is:

1. A water-monitoring apparatus comprising:
   a frame (19) being installed by water;
   a reel (10) being mounted on the frame (19);
   a cable (15) being wound on the reel (10) and including a lower end and an upper end;
   a buoy (30) being connected with the cable (15);
   a control device being connected with the reel (10) wherein when the water
   level changes, the control device rotates the reel (10) so as to adjust a length of the cable (15) extending from the reel (10) for allowing the buoy (30) to just float on the water surface;
   a detecting device being carried via the buoy (30) and electrically connected with the lower end of the cable (15) for detecting at least one environmental characteristic and for producing at least one signal representative of the at least one environmental characteristic; and
   a signal relay (20) being electrically connected between the detecting device and a monitoring station.

2. The water-monitoring apparatus as set forth in claim 1 wherein the control device is a constant torque device for exerting a constant torque on the reel (10).

3. The water-monitoring apparatus as set forth in claim 2 wherein the constant torque device is a coil spring (13) including a first end attached to the frame (19) and a second end attached to the reel (10).

4. The water-monitoring apparatus as set forth in claim 2 comprising a shaft (11) mounted on the frame (19), the reel (10) being mounted on the shaft (11).

5. The water-monitoring apparatus as set forth in claim 4 wherein the constant torque device is a coil spring (13) including a first end attached to the shaft (11) and a second end attached to the reel (10).

6. The water-monitoring apparatus as set forth in claim 2 wherein the constant torque device is a constant torque spring assembly (50).

7. The water-monitoring apparatus of claim 6 wherein the shaft (51) is mounted on the frame (19) in a rotational manner and the constant torque spring assembly (50) comprises:
   a first drum (53) being connected with on the shaft (51) so that they can rotate together;
   a second drum (53) being rotationally mounted on the frame (19); and
   a spring wound on the first drum (53) and the second drum (53).

8. The water-monitoring apparatus as set forth in claim 1 wherein the signal relay (20) is a non-contact signal relay.

9. The water-monitoring apparatus as set forth in claim 8 wherein the non-contact signal relay (20) comprises first and second blocks electrically connected with each other in a non-contact manner.

10. The water-monitoring apparatus as set forth in claim 9 wherein the first block is electrically connected with the detecting device and the second block is electrically connected with the monitoring station.

11. The water-monitoring apparatus as set forth in claim 1 wherein the detecting device includes at least one sensor (35) for producing at least one primary signal representative of a water quality parameter.

12. The water-monitoring apparatus as set forth in claim 11 wherein the detecting device includes a sensor control board (33) for converting the primary signal to an electric signal.

13. The water-monitoring apparatus as set forth in claim 12 wherein the signal relay (20) is a non-contact signal relay.

14. The water-monitoring apparatus as set forth in claim 13 wherein the non-contact signal relay (20) comprises first and second blocks electrically connected with each other in a non-contact manner.

15. The water-monitoring apparatus as set forth in claim 14 wherein the first block is electrically connected with the sensor control board (33) and the second block is electrically connected with the monitoring station.

16. The water-monitoring apparatus as set forth in claim 15 wherein:
   the first block includes:
      a first circuit board (21) being attached to the reel (10); and
      an emitter (24) being formed on the first circuit board (21) for emitting the signals, and
   the second block includes:
      a second circuit board (26) being attached to the frame (19) and electrically connected with a monitoring station; and
      a receiver (28) being formed on the second circuit board (26) for receiving the signals.

17. The water-monitoring apparatus as set forth in claim 16 wherein the emitter (24) is a light emitter for emitting an optical signal and the receiver (28) is a light receiver for receiving the optical signal.

18. The water-monitoring apparatus as set forth in claim 17 wherein the first circuit board (21) is used to transform the electric signal into the optical signal for emission via the light emitter (24).

19. The water-monitoring apparatus as set forth in claim 17 wherein the second circuit board (26) is used to transform the optical signal received via the light receiver (28) into an electric signal.

20. The water-monitoring apparatus as set forth in claim 16 wherein the signal relay (20) comprises a connector (22) formed on the first circuit board (21) for electric engagement with the upper end of the cable (15).

21. The water-monitoring apparatus as set forth in claim 12 wherein the sensor control board (33) is received in the buoy (30).

22. The water-monitoring apparatus as set forth in claim 12 wherein the sensor control board (33) periodically acquires signals from the sensors and is kept in a power-saving mode for the rest of the time.

23. The water-monitoring apparatus as set forth in claim 16 wherein the signal relay (20) comprises a power supply installed on the first circuit board (21).

24. The water-monitoring apparatus as set forth in claim 23 wherein the power supply is a battery (23) installed on the first circuit board (21).

25. The water-monitoring apparatus as set forth in claim 24 wherein the battery (23) provides power to the sensor control board (33) through the cable (15).

26. The water-monitoring apparatus as set forth in claim 16 wherein the signal relay (20) comprises a button (25) formed on the first circuit board (21), and the button (25) can be pressed in order to actuate the sensor control board (33).

27. The water-monitoring apparatus as set forth in claim 16 wherein the sensor control board (33) and the first circuit board (21) are merged into one.

28. The water-monitoring apparatus as set forth in claim 1 comprising a level-determining device for determining the water level.

29. The water-monitoring apparatus as set forth in claim 28 wherein the level-determining device includes a pulley (40) mounted on the frame (19), a length of the cable (15) being wound on the pulley (40) so that the cable (15) rotates the pulley (40) as the buoy (30) rises or falls.

30. The water-monitoring apparatus as set forth in claim 29 wherein the level-determining device includes:

a number of magnets (41) evenly arranged near or on the periphery of the pulley (40), wherein when the water level changes, the buoy (30) moves, thus causing the pulley (40) to rotate and the magnets (41) to move in a direction; and a magnetic detector (45) mounted on the frame (19) for detecting each magnet (41) passing by, wherein the magnetic detector (45) determines how much the water level rises or falls by detecting how many magnets (41) pass by and in what direction.

31. The water-monitoring apparatus as set forth in claim 30 wherein the level-determining device includes a second pulley (42) mounted on the frame (19) so that the cable (15) can be wound on the pulley (42).

32. The water-monitoring apparatus as set forth in claim 1 wherein the detecting device includes a number of sensors each for producing a primary signal representative of a water quality parameter.

\* \* \* \* \*